United States Patent [19]

Crouther et al.

[11] 4,308,232
[45] Dec. 29, 1981

[54] ANTICOAGULANT STOPPER COATING

[75] Inventors: Ronald Crouther, Manchester; Fred E. Satchell, Chesterfield; Glen Stone, O'Fallon, all of Mo.

[73] Assignee: Sherwood Medical Industries Inc., St. Louis, Mo.

[21] Appl. No.: 55,566

[22] Filed: Jul. 9, 1979

[51] Int. Cl.³ .............................................. A61J 1/00
[52] U.S. Cl. .................................... 422/102; 210/927; 422/101; 427/379; 427/417; 428/447; 128/272
[58] Field of Search ............... 210/500 M, DIG. 23, 210/DIG. 24, 927; 23/230 B; 424/83, 82, 78, 183; 428/492, 447, 422, 522, 523; 260/9, 17.4 R; 128/272 422/101, 102; 427/379, 417

[56] References Cited

U.S. PATENT DOCUMENTS

| | | | |
|---|---|---|---|
| 3,617,344 | 11/1971 | Leininger | 428/447 |
| 3,634,123 | 1/1972 | Eriksson | 424/183 |
| 3,673,612 | 7/1972 | Merrill et al. | 424/82 |
| 3,810,781 | 5/1974 | Eriksson et al. | 424/183 |
| 3,882,021 | 5/1975 | Ayres | 210/136 |
| 3,958,572 | 5/1976 | Lawhead | 128/272 |
| 4,116,898 | 9/1978 | Dudley et al. | 424/83 |
| 4,118,485 | 10/1978 | Eriksson et al. | 424/183 |

*Primary Examiner*—Ivars C. Cintins

[57] ABSTRACT

A stopper for a blood collection tube adapted to receive whole blood for centrifugal separation into its relatively light and heavy phases. The stopper is provided with a coating which prevents red blood cells from adhering to it so as to avoid red cell contamination of the lighter phase after phase separation. The stopper is coated with a cationic binding agent, such as tridodecylmethylammonium chloride, and then with an anionic anticoagulant such as dextran sulfate. A lubricant, such as silicone oil, is applied to the coated stopper to facilitate insertion of the stopper into the tube.

33 Claims, 2 Drawing Figures

ANTICOAGULANT STOPPER COATING

BACKGROUND OF THE INVENTION

This invention relates to blood collection devices and, more particularly, to the reduction of cell contamination of the separated lighter blood phase in a blood collection device.

It is common practice to employ a collection tube for receiving a whole blood sample from a patient whose blood is to be clinically tested, and then to centrifuge the filled tube to separate the blood into its lighter phase, serum or plasma, and its heavier cellular phase. In some cases, well known automatic or centrifugally activated phase partitioning devices or materials are placed in the tube which provide a liquid-impervious barrier between the separated phases after centrifugation. The barrier maintains the light phase isolated from the cellular phase components and facilitates subsequent removal of the light phase from the tube free of red cells.

However, red blood cells often adhere to surfaces of the stopper within the tube after the phases have been separated so that such cells remain in that portion of the tube which contains the separated lighter phase. These cells may come in contact with the light phase during handling or during removal of the stopper and light phase from the collection tube, and can contaminate the light phase such that some clinical tests performed produce inaccurate and unreliable results.

In an attempt to prevent blood cells from adhering to the stopper, the stopper has been shaped so that cells contacting it will have a tendency to to slide off. However, such shaping of the stopper has not been entirely satisfactory. U.S. Pat. No. 3,958,572 illustrates a stopper shaped to reduce the chance of cells adhering to the inner side of the stopper. This method requires a special stopper construction and still does not insure against the adherence of cells to the stopper. It is also mentioned in that patent that if the stopper is made of rubber, then silicone oils or glycerine solutions can be used as lubricants for easy insertion and removal of the stopper, and that such treatment also gives added protection against cell or clot adherence to the stopper. However, coating stoppers with a lubricant has generally not been an effective solution to the prevention of cell adherence to the stopper and cell contamination of the light phase.

In U.S. Pat. No. 3,882,021, a phase partitioning piston remains in its initial position and is sealed against contact with the blood by a frangible seal to prevent contamination of the piston by blood cells during phase separation. Upon increased centrifugal force, after phase separation, the seal is broken and moves to the bottom of the tube, and the piston slides to a position adjacent the interface of the light and heavy phases. This device employs a relatively expensive tube assembly having a stopper in each end. It also requires the operator to centrifuge the tube at one speed until phase separation has taken place, and then to increase the speed in order to break the frangible seal. Thus, such a frangible seal arrangement results in a rather complicated separation procedure and a relatively expensive device.

SUMMARY OF THE INVENTION

It is therefore an object of the present invention to provide a collection device wherein the above-mentioned disadvantages are substantially obviated. Another object of the present invention is to provide a stopper for a blood collection device which is effective in preventing the adherence of blood cells to it. Still another object is to provide a method of treating a blood collection tube stopper so that the tendency of blood cells to adhere to it is greatly reduced.

In accordance with one aspect of the present invention, a closure for a blood collection container is provided with a layer of a binding agent, and a layer of an anticoagulant which adheres to the binding agent to prevent cell adhesion on the stopper.

These and other objects and advantages of the present invention will become apparent from the detailed description and accompanying drawing.

DESCRIPTION OF THE PREFERRED EMBODIMENT

Figures 1, 2:
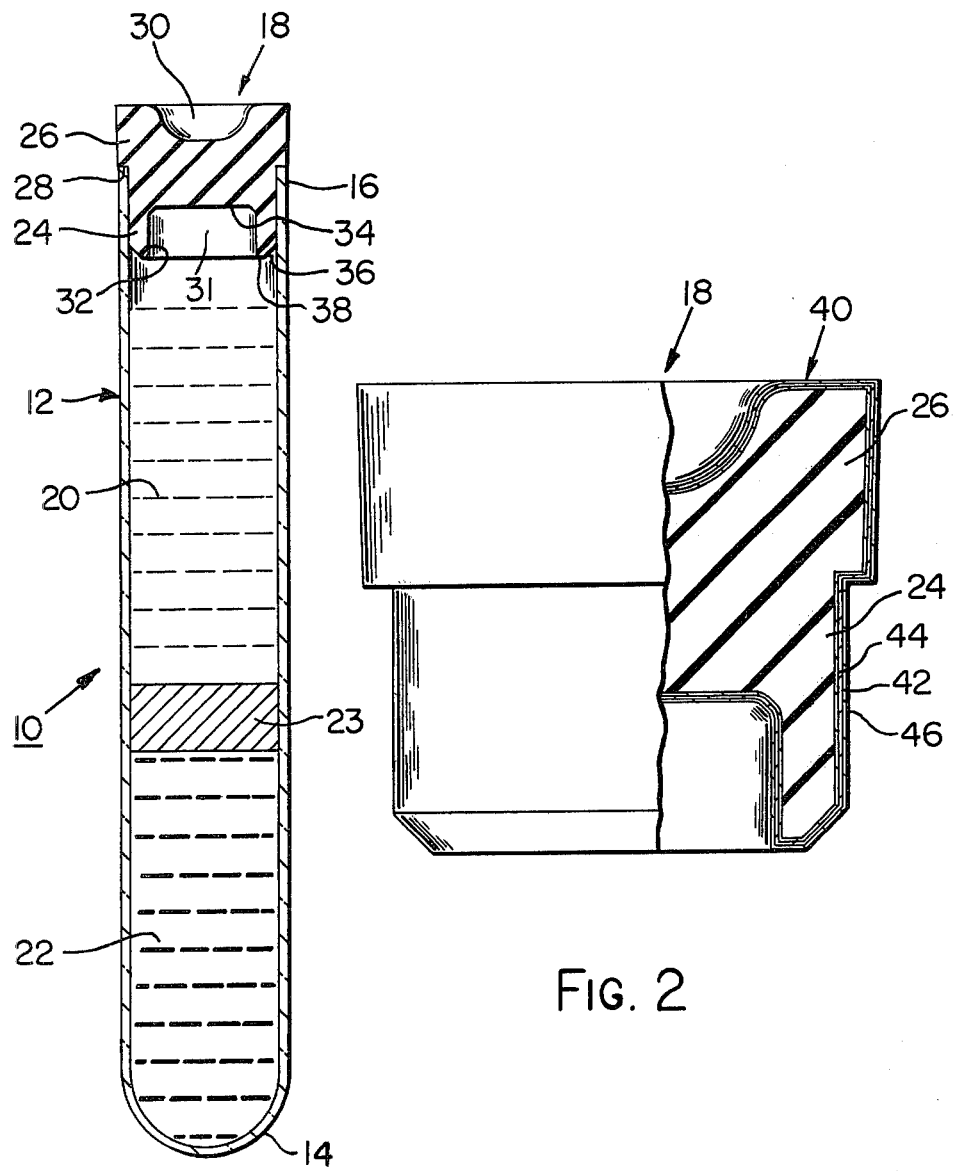
FIG. 1 is an elevational view in cross-section of a blood collection device employing a coated stopper in accordance with a preferred embodiment of the present invention and illustrating the device containing separated relatively light and heavy blood phases.
FIG. 2 is an enlarged view of the stopper of FIG. 1 partly broken and in cross-section and showing the stopper coating in exaggeration.

Referring now to the drawing, and particularly to FIG. 1, a blood collection device 10 is shown including a blood collection container or tube 12 closed at the bottom, such as by an integral end portion 14, and having an open upper end 16 closed by a stopper 18 made in accordance with the present invention and which will be described in detail hereafter. The stopper 18 is formed of a suitable elastomer or rubber, such as a conventional butyl rubber composition, and is pierceable by a needle cannula for the purpose of introducing a whole blood sample into the tube from a patient. Stopper 18 is self-sealing at the point at which it is pierced when the cannula is removed. Tube 12 is preferably of glass and provided with a partial vacuum which is maintained by stopper 18 until the tube is used.

Various reagents, depending upon the particular test to be conducted, may be provided in the tube. An anticoagulant, such as heparin or dextran sulfate, may be provided in the tube where plasma is to be obtained. Clot activating particles may be provided to decrease the clotting time when serum is to be obtained.

In FIG. 1, the collection device 10 is shown after a whole blood sample has been taken into the tube 12 and after the device has been centrifuged. The blood is indicated as being separated into its relatively light or less dense phase indicated at 20, and its heavy or more dense cellular phase, indicated at 22. Also, shown in the tube 12 is a phase barrier or partition 23 formed of a well-known, inert, thixotropic gel-like material. For example, the barrier 23 may be formed of a suitable mixture of silicone oil and silica powder as disclosed in U.S. Pat. No. 3,852,194 or a suitable mixture of polybutene and silica powder as disclosed in U.S. Pat. No. 4,021,340. The gel-like material is made to have a specific gravity between the specific gravities of the separated phases, for example, it may be made so that it has a 1.05 specific gravity. In this way, it moves from its original position in the tube, such as in the bottom, to the shown location between the separated light and heavy phases 20 and 22. Other types of automatic or centrifugally actuated phase separators are well-known and may be used instead of the gel-like material illustrated.

Stopper 18 is shown in FIG. 1 including a plug portion 24 disposed in tube 12 to sealingly close the upper end 16, and an enlarged upper portion or head 26 forming a shoulder 28 which engages the upper edge of the tube and limits the inward movement of the stopper during insertion. The stopper 18 has a central outer recess 30 in its outer upper surface and a central inner recess 31 in its bottom surface within tube 12. The recesses 30 and 31 reduce the cross-section or axial dimension of the stopper at its center to facilitate the penetration of the stopper by a needle.

The bottom surface of stopper 18 is, of course, subject to being contacted by whole blood during the drawing of the sample and during handling of the filled tube 12. The bottom surface of the stopper includes recess 31 having side walls 32 and a bottom wall 34, annular beveled leading surface 36, and an annular flat bottom end surface 38 that connects the beveled surface 36 with the side walls 32. The leading surface 36 is, of course, beveled to facilitate the insertion of the stopper into the tube during manufacture.

When using conventional stoppers that are merely coated with a lubricant, cells often adhere to the bottom surface of the stopper and especially to the beveled surfaces and the side walls of the inner recess. During handling of such devices, the lighter phase may come in contact with such cells, with the cells contaminating the light phase so that test results may be inaccurate. Also, in conventional blood collection devices, when the stopper is removed from the tube 12, some cells that adhered to the stopper may fall into the light phase. In accordance with the present invention, stopper 18 is treated or coated such that cells substantially do not adhere to surfaces of the stopper within tube 12. Preferably, stopper 18, for convenience, is treated or coated over its entire surface by a coating 40, indicated in exaggeration in FIG. 2.

The major constituents of the stopper coating 40 are a blood anticoagulant, shown as a layer 42, and a binding agent layer 44 which tenaciously binds the anticoagulant to the stopper. An outer layer 46 is a suitable lubricant, preferably silicone oil, which may be applied over the anticoagulant layer 42 to facilitate insertion of the stopper into the tube 12. Instead of silicone oil, other known lubricants, such as glycerine, can be used.

The binding agent 44 for anticoagulant layer 42 is a cationic surfactant, preferably a quaternary ammonium surfactant or salt tridodecylmethylammonium chloride (TDMAC). The TDMAC is applied as a solution in organic solvents such as toluene and petroleum ether, for example, in a 50%—50% mixture of the two solvents. The nonpolar portion of the TDMAC molecule has an affinity for the nonpolar rubber surface of the stopper so that good bonding occurs. Also, the solvents swell the rubber surface and the TDMAC molecules can embed themselves in the stopper surface so that the TDMAC is tightly bound to the surface of the stopper. Other binding agents such as other cationic surfactant binding agents, for example, tridecylmethylammonium chloride or trioctalmethylammonium chloride may be used.

The anticoagulant layer 42, which is the active portion of the coating 40, is an anionic anticoagulant such as dextran sulfate which is a polymeric anticoagulant salt. The dextran sulfate is applied in an aqueous solution to the TDMAC-coated stopper after the TDMAC layer 44 is dry, as will be discussed hereinafter. The cationic (nitrogen atom) portion of the TDMAC molecule, because it carries a positive charge, is attracted to the negatively charged portion of the dextran sulfate molecules which are primarily the sulfate groups. Thus, the dextran sulfate which is soluble in water or blood when free binds itself to the TDMAC layer and becomes less soluble in whole blood.

Because of the good bonding between the TDMAC and the stopper, and between the dextran sulfate and the TDMAC, the dextran sulfate layer does not dissolve away into the blood sample so that it remains on the stopper preventing or greatly reducing cell adhesion to the stopper. Also, because the dextran sulfate layer does not dissolve away into the blood sample, it does not act as an anticoagulant in the blood sample. This is especially important where it is desired to coagulate the sample and obtain serum.

After the TDMAC and dextran sulfate layers have been applied and dried, the outer lubricant layer 46 of silicone oil is applied. The tube 12 is provided with the partitioning material and/or any other material desired, and then the stopper is inserted into the upper end 16 of tube 12. The stopper is inserted with the tube 12 in a vacuum where it is desired to have a negative pressure in the tube.

The dextran sulfate layer minimizes the adherence of red blood cells to the stopper surface. It is believed that the negatively charged sulfate groups present on the molecule repel red blood cells which have a small negative charge present on their surfaces. The lubricant may have some red blood cell repelling effect also.

A preferred TDMAC solution includes about 0.325 grams of TDMAC per 100 ml of solvent, the solvent being a 50%—50% mixture of a petroleum ether and toluene. The concentration of the solution may vary somewhat from 0.325 grams TDMAC/ml solvent; solutions of 0.1 gram/ml and 0.8 gram/ml have been found satisfactory.

Preferably, a high molecular weight dextran sulfate is utilized. A suitable aqueous solution of dextran sulfate is one having about 82 units of heparin activity/ml. If the solution has a heparin activity too great, for example, 160 units of heparin activity per ml was found excessive in one case, it will undesirably tend to dissolve in the blood and prevent or retard blood coagulation, and this is undesirable, of course, where it is desired to coagulate the blood and obtain serum. If a dextran sulfate solution has an excessively low heparin activity, for example, below 15 units of heparin activity/ml has been found to be low in some cases, it will tend to be less effective in repelling red blood cells from the stopper.

The process of coating the stoppers may generally include immersing a quantity of the stoppers in a suitable cationic binding agent solution such as the above-described preferred TDMAC solution. The stoppers are removed from the solution and allowed to fully dry. The TDMAC-coated stoppers are then dipped in the aqueous dextran sulfate solution and then removed and dried. The lubricant is then applied to the coated stoppers.

In one example process, clean stoppers were immersed for about 15 seconds in the preferred TDMAC solution, removed from the solution, and excess solution on the stoppers blown off with deionized air. The stoppers were then allowed to dry for about one hour in an atmosphere of approximately 25° C.

Next, the TDMAC-coated stoppers were immersed for about 15 seconds in the preferred, above-described, aqueous dextran sulfate solution. The stoppers were removed and the excess dextran sulfate solution on the stoppers was blown off with deionized air. The dextran sulfate-coated stoppers were then placed in a 100° C. oven for two hours to dry and age. The coated stoppers were then cooled to room temperature.

The dextran sulfate-coated stoppers were then lubricated by placing them in a drum with a relatively small amount of silicone oil disposed on the drum. For example, about five drops of oil per 50 stoppers was found satisfactory. The stoppers were tumbled in the drum until they had a thin coating of oil on them.

It was found that the above artificial aging of the dextran sulfate-coated stoppers in the 100° C. oven enhanced their effectiveness in repelling cells or inhibiting blood cell adhesion. The temperature and length of time of the drying and aging steps can vary.

The coated and lubricated stoppers can then be employed to seal the open ends of blood collection tubes while in a partial vacuum.

Stoppers treated in the above-described manner significantly inhibit the adherence of red cells thereto and reduce red cell contamination of the light phase.

As various changes could be made in the above-described construction and method without department from the scope of the invention, it is intended that all matter contained in the above description and shown in the accompanying drawing be interpreted as illustrative and not in a limiting sense.

What is claimed is:

1. A stopper for a blood collection container capable of sealingly closing one end of the container with a bottom surface thereof facing the opposed end of the container comprising an elastomeric closure member, a first layer of a binding agent covering said bottom surface, and a second layer including dextran sulfate bonded to and covering said first layer to inhibit adherence of red blood cells to said closure member when contacted by blood.

2. The stopper of claim 1 wherein said binding agent is a cationic surfactant.

3. The stopper of claim 1 wherein said binding agent is a quaternary ammonium surfactant.

4. The stopper of claim 3 wherein said binding agent is tridodecylmethylammonium chloride.

5. The stopper of claim 1 further including a layer of a lubricant covering at least said second layer.

6. The stopper of claim 1 wherein the stopper includes a plug portion having an annular sealing surface, and a lubricant on at least said sealing surface.

7. The stopper of claim 1 wherein said binding agent is a quaternary ammonium salt, said binding agent layer covers substantially the entire surface of said member, and said second layer covers substantially the entire binding agent layer.

8. In a blood collection device including a blood collection tube, and a stopper closing one end of the tube, the improvement comprising a first layer of a cationic surfactant binding agent on at least the bottom surface of the stopper within the tube, a second layer including dextran sulfate covering said first layer and being bound to said first layer such that it is substantially insoluble in whole blood, said second layer inhibiting adherence of red blood cells to the stopper during use of the device.

9. The device of claim 8 wherein said first layer includes tridodecylmethylammonium chloride.

10. The device of claim 1 or 9 wherein the stopper has a lubricant coating said second layer.

11. The device of claim 10 wherein said lubricant is a silicone oil.

12. The device of claim 1 or 9 wherein said first layer covers substantially the entire outer surface of the stopper, said second layer covers substantially the entire outer surface of said first layer.

13. The device of claim 12 wherein a lubricant covers substantially the entire outer surface of said second layer.

14. The device of claim 13 wherein the tube has a partial vacuum therein, and the stopper is pierceable by a needle cannula for introducing whole blood into the tube.

15. The device of claim 14 wherein the stopper comprises a material including butyl rubber.

16. The stopper of claim 1 or 8 wherein said second layer has a heparin activity that substantially does not effect an increase in the clotting time of blood when disposed in the container during use thereof.

17. The method of treating an elastomeric closure stopper for a blood collection container to inhibit the adhesion of red blood cells thereto during use comprising the steps of coating at least that portion of the stopper that is subject to come in contact with blood with a solution of a binding agent, drying the stopper to effect a dry binding agent layer, coating the binding agent layer with a solution including dextran sulfate, and drying the stopper to effect a dried layer including dextran sulfate bonded to the binding agent layer, to inhibit red blood cell adhesion to the stopper when contacted by blood.

18. The method of claim 17 wherein said binding agent and said dextran sulfate are cationic and anionic, respectively.

19. The method of claim 17 wherein said binding agent includes a quaternary ammonium salt.

20. The method of claim 19 wherein said binding agent is tridodecylmethylammonium chloride.

21. The method of claim 17 or 20 further including the step of applying a coating of a lubricant over said dextran sulfate layer.

22. The method of claim 17 wherein the binding agent solution includes a quaternary ammonium salt and a solvent for said salt.

23. The method of claim 22 wherein the binding agent solution comprises the quaternary ammonium salt in a range between about 0.1 to about 0.8 grams per milliliter of solvent.

24. The method of claim 23 wherein about 0.3 grams of quaternary ammonium chloride per milliliter of solvent is used to form the binding agent solution.

25. The method of claim 24 wherein the quaternary ammonium chloride is tridodecylmethylammonium chloride.

26. The method of claim 25 wherein the solvent includes petroleum ether and toluene.

27. The method of claim 26 wherein the solvent has approximately equal amounts of petroleum ether and toluene.

28. The method of claim 17 or 22 wherein the solution including dextran sulfate has heparin units of activity which are more than 15 units and less than 160 units.

29. The method of claim 17 wherein said dried dextran sulfate layer is aged in an oven at a temperature above the ambient.

30. The method of claim 17 wherein said solution including dextran sulfate further includes water.

31. The method of claim 30 further including the step of applying a lubricant to cover the dried dextran sulfate layer.

32. The method of claim 31 wherein each of the steps of applying said binding agent solution and said solution including dextran sulfate include immersing the stopper in said solutions.

33. The method of claim 17 wherein the solution including dextran sulfate has approximately 80 heparin units of activity.

* * * * *